(12) United States Patent
Lam et al.

(10) Patent No.: US 11,495,438 B2
(45) Date of Patent: Nov. 8, 2022

(54) PLASMA TREATING AN IMPLANT

(71) Applicant: NOVA PLASMA LTD., Hevel Megiddo (IL)

(72) Inventors: Amnon Lam, Kibbutz Givat Oz (IL); Eliezer Fuchs, Kibbutz Megido (IL); Aviad Harhol, Ramat Hasharon (IL)

(73) Assignee: NOVA PLASMA LTD., Hevel Megiddo (IL)

( * ) Notice: Subject to any disclaimer, the term of this patent is extended or adjusted under 35 U.S.C. 154(b) by 445 days.

(21) Appl. No.: 16/639,037

(22) PCT Filed: Aug. 16, 2018

(86) PCT No.: PCT/IL2018/050909
§ 371 (c)(1),
(2) Date: Feb. 13, 2020

(87) PCT Pub. No.: WO2019/035135
PCT Pub. Date: Feb. 21, 2019

(65) Prior Publication Data
US 2020/0185197 A1    Jun. 11, 2020

Related U.S. Application Data

(60) Provisional application No. 62/546,013, filed on Aug. 16, 2017.

(51) Int. Cl.
*H01J 37/32* (2006.01)
*A61L 2/14* (2006.01)
*A61F 2/12* (2006.01)

(52) U.S. Cl.
CPC .......... *H01J 37/32403* (2013.01); *A61L 2/14* (2013.01); *H01J 37/32082* (2013.01); *H01J 37/32449* (2013.01); *A61F 2/12* (2013.01)

(58) Field of Classification Search
CPC .......... H01J 37/32082; H01J 37/32403; H01J 37/32449; H01J 37/32798
See application file for complete search history.

(56) References Cited

U.S. PATENT DOCUMENTS 3,851,436 A    12/1974   Fraser
4,846,101 A    7/1989    Montgomery
(Continued)

FOREIGN PATENT DOCUMENTS

CN    101711708 A    5/2010
JP    2008515616 A   5/2008
(Continued)

OTHER PUBLICATIONS

Duske et al., (2012) Atmospheric plasma enhances wettability and cell spreading on dental implant metals. Journal of Clinical Periodontology 39(4): 400-407.
(Continued)

*Primary Examiner* — Tung X Le
(74) *Attorney, Agent, or Firm* — Dorsey & Whitney LLP

(57) ABSTRACT

A method is provided for treating an implant in a medical care center prior to using the implant in a medical procedure. The method comprises applying a plasma-generating electromagnetic (EM) field using at least one electrode so as to generate plasma in a vicinity of the implant while displacing the electrode and the implant relative to one another. A portable plasma module and a docking station configured to connect to the portable plasma module, thereby forming a plasma generating system, are also provided. A plasma generating apparatus for treating an implant prior to using the implant in a medical procedure is also provided.

21 Claims, 5 Drawing Sheets

(56) References Cited

U.S. PATENT DOCUMENTS

| | | |
|---|---|---|
| 4,955,901 A | 9/1990 | Nishiguchi |
| 5,188,800 A | 2/1993 | Green, Jr. |
| 5,558,230 A | 9/1996 | Fischer |
| 5,697,997 A | 12/1997 | Aronsson |
| 5,960,956 A | 10/1999 | Langanki |
| 6,033,437 A | 3/2000 | Perry |
| 6,702,855 B1 | 3/2004 | Steinemann |
| 7,451,870 B2 | 11/2008 | Donahoe |
| 8,071,042 B2 | 12/2011 | Kuhry |
| 8,190,271 B2 | 5/2012 | Overstreet |
| 8,518,420 B2 | 8/2013 | Biris |
| 2004/0037946 A1 | 2/2004 | Morra |
| 2004/0150386 A1* | 8/2004 | Gonzalez .......... H01J 37/32174 324/117 R |
| 2005/0031689 A1 | 2/2005 | Shults |
| 2005/0035015 A1 | 2/2005 | Bressler |
| 2006/0251795 A1 | 11/2006 | Kobrin |
| 2007/0084144 A1 | 4/2007 | Labrecque |
| 2007/0225785 A1 | 9/2007 | Park |
| 2008/0208347 A1 | 8/2008 | Muratoglu |
| 2008/0289576 A1* | 11/2008 | Lee .................. H01J 37/3244 118/723 I |
| 2008/0296510 A1* | 12/2008 | Kasama ............ H01J 37/32412 250/492.3 |
| 2009/0192528 A1 | 7/2009 | Higgins |
| 2010/0047532 A1 | 2/2010 | Mozetic |
| 2010/0237043 A1 | 9/2010 | Garlough |
| 2011/0008877 A1 | 1/2011 | Skelnik |
| 2011/0095688 A1 | 4/2011 | Bisges |
| 2012/0183437 A1 | 7/2012 | Keener |
| 2012/0217221 A1* | 8/2012 | Hoffman .................. C23C 16/50 216/61 |
| 2013/0118406 A1 | 5/2013 | Rostaing |
| 2013/0230426 A1 | 9/2013 | Popot |
| 2014/0224687 A1 | 8/2014 | Schuster |
| 2014/0377320 A1 | 12/2014 | Pietramaggiori |
| 2016/0000062 A1 | 1/2016 | Chen |
| 2016/0264274 A1 | 9/2016 | Kulaga |
| 2016/0331841 A1 | 11/2016 | Prestwich |
| 2017/0014553 A1 | 1/2017 | Antoni |
| 2019/0099259 A1 | 4/2019 | Porter |
| 2019/0365527 A1 | 12/2019 | Wijay |

FOREIGN PATENT DOCUMENTS

| | | |
|---|---|---|
| WO | 9312821 A1 | 7/1993 |
| WO | 0014146 A1 | 3/2000 |
| WO | 2007103705 A2 | 9/2007 |
| WO | 2013056844 A1 | 4/2013 |
| WO | 2015083155 A1 | 6/2015 |
| WO | 2015087326 A1 | 6/2015 |
| WO | 2015091104 A1 | 6/2015 |
| WO | 2016062763 A1 | 4/2016 |
| WO | 2016181396 A1 | 11/2016 |

OTHER PUBLICATIONS

Heinlin et al., (2010) Plasma medicine: possible applications in dermatology. JDDG: Journal der Deutschen Dermatologischen Gesellschaft 8(12): 968-976.

Lee et al., (2011) Improvement of Hydrophilicity of Interconnected Porous Hydroxyapatite by Dielectric Barrier Discharge Plasma Treatment. IEEE Transactions on Plasma Science 39(11): 2166-2167.

Moriguchi et al., (2012) Plasma Surface Modification of Artificial Bones for Bone Regeneration. Orleans-France, 48. 1 page.

CeraPlas™ piezo plasma generator. Cold plasma from a single component; Oct. 31, 2014. Retrieved from: https://en.tdk.eu/tdk-en/373562/tech-library/articles/applications—cases/applications—cases/cold-plasma-from-a-single-component/1109546. © TDK Electronics AG; 6 pages.

* cited by examiner

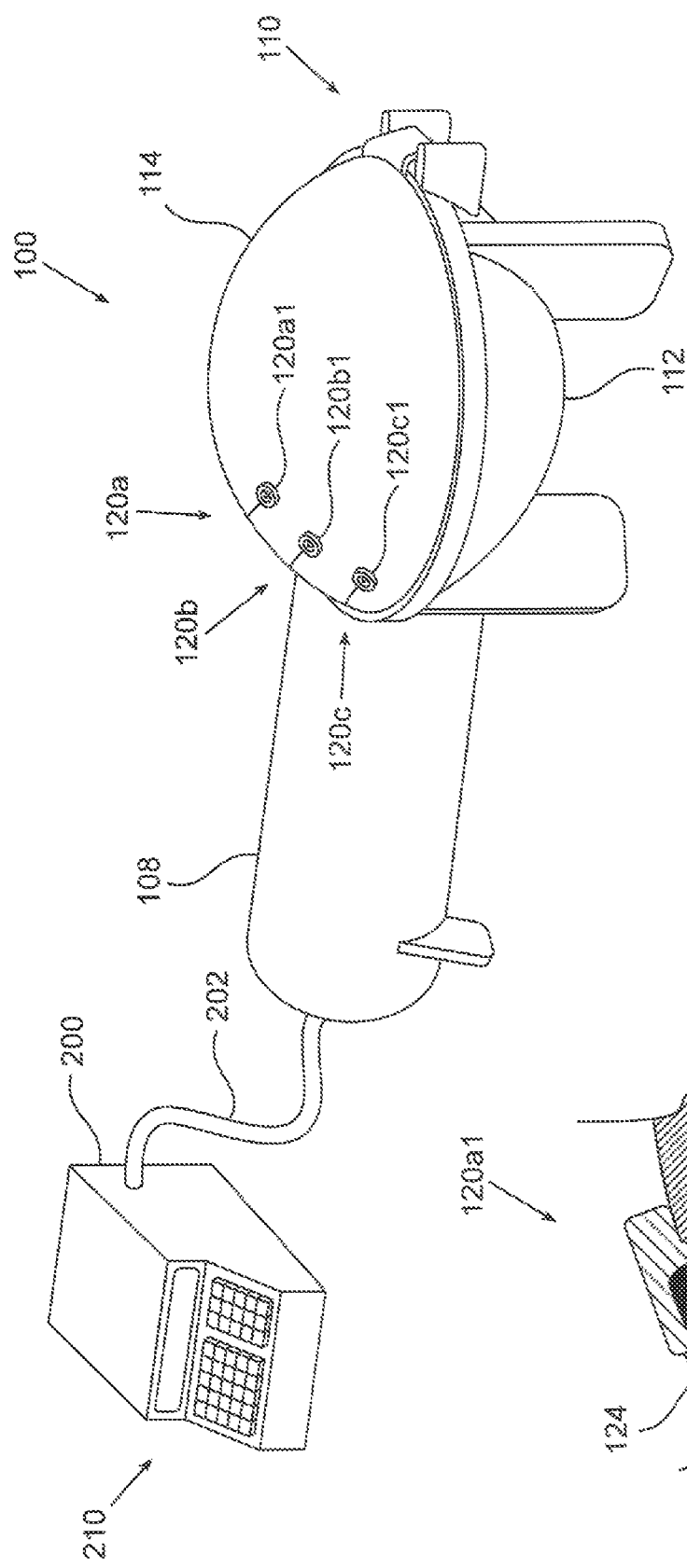
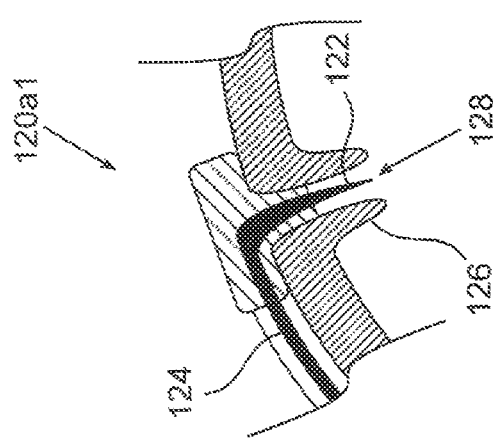
Fig. 1A
Fig. 1B

PLASMA TREATING AN IMPLANT

FIELD OF THE INVENTION

The invention, in some embodiments, relates to the field of handling and plasma-treating an implant, and more specifically, but not exclusively, plasma treating a dielectric implant such as a breast implant, prior to using the implant in a body of a live subject, and to related systems, apparatuses and methods.

BACKGROUND OF THE INVENTION

Plasma is known to affect surfaces of objects that are exposed to the plasma. Generally, plasma refers herein to ionized gas, including positively charged ions and negatively charged electrons, wherein the whole volume of the ionized gas is roughly neutral. Positively charged ions are generally referred to herein simply as "ions", negatively charged electrons are referred to as "electrons", and neutral atoms and molecules are referred to as "neutrals".

Surfaces of objects exposed to plasma may often be affected so that some characteristics of the surface change following such exposure. It is believed that surface energy and chemistry may change due to the generation of reactive species in the plasma, and possibly due to deposition of chemical substances on the surface. A featured result may be a modification of the surface properties. For example, plasma generated in a gaseous atmosphere comprising argon or helium possibly with an admixture of oxygen, or in air at low pressure or at atmospheric pressure, may render a surface of an object more hydrophilic.

International patent application WO2015/087326 to Lam et al. (herein Application '326), filed on Dec. 10, 2014, discloses a portable container for handling an implant. The portable container comprises a sealed compartment enclosing a fluid of a pre-defined composition and at least one implant configured to be installed in a live subject. The portable container may further comprise at least one electrode, electrically associated with an electric conductor outside the sealed compartment and configured for applying a plasma generating electric field inside the sealed compartment. An apparatus for plasma treatment of an implant and having an activation device is further provided. The activation device comprises a slot configured to receive a portable container, and an electrical circuit configured to be electrically associated with at least one electrode. The electrical circuit is configured to provide to the at least one electrode electric power suitable for applying a plasma generating electric field in the sealed compartment, when the portable container is disposed in the slot. According to some embodiments, the portable container is dimensioned and configured to contain a breast implant in the sealed compartment.

International patent application WO2016/181396, to Lam et al. (herein Application '396), filed on May 11, 2016, discloses an apparatus for plasma treatment of an implant prior to installing the implant in a live subject. The apparatus comprises an activation device and a portable container detachable from the activation device. The portable container comprises a closed compartment containing the implant immersed in a fluid, and the activation device comprises a slot configured to receive the portable container. The activation device further comprises an electrical circuit configured to be electrically associated with at least one electrode and configured to provide to the at least one electrode electric power suitable for applying a plasma generating electric field in the closed compartment, when the portable container is disposed in the slot. A container suitable for providing plasma treatment to a silicone implant, such as a breast implant, and a method for preparing an implant for implantation surgery are also provided. Applications '326 and '396 are fully incorporated herein by reference.

SUMMARY OF THE INVENTION

Aspects of the invention, in some embodiments thereof, relate to handling and plasma-treating an implant, prior to using the implant in a body of a live subject. More specifically, but not exclusively, aspects of the invention relate to plasma treating a dielectric implant such as a silicone breast implant, and to related devices, apparatuses and methods.

If an object intended to be installed in a body of a live subject is exposed to plasma under certain conditions, biocompatibility of the object tends to improve. Such biocompatibility, associated with surface properties of the object, may include higher wettability, more suitable topography and improved drug delivery. For example, following suitable plasma treatment of an implant, hydrophilic properties of the surface of the implant tend to improve. Hydrophilic properties substantially enhance the wettability of the surface and improve the initial attachment of blood platelets to the treated implant. Consequently, better healing process may be achieved with substances that have been exposed to plasma prior to use.

Better healing process may be achieved with implants that have been exposed to plasma prior to installing. For example, plasma surface treatment often improves biocompatibility of polystyrene cell culture surfaces, affecting adhesion and proliferation of cells cultures on such surfaces. For example, plasma surface modification of cell-culture materials may assist in establishing a stable culturing process for cells obtained from a patient's own body, for a later regeneration medicine process with the patient. Further, Application '396 teaches a method for preventing or minimizing risk of contamination following implantation by plasma-treating a silicone implant such as a breast implant, and possibly wetting the implant with a polar liquid following such treatment.

Notwithstanding the beneficial effects of plasma treatment discussed above, such beneficial effects of exposure to plasma on implant surfaces are often temporary, particularly if the implant is maintained in air after the treatment. Demonstrated improved or enhanced healing decreases as the time interval increases, between exposure of the implant to plasma and installing the implant in a body. Such temporal deterioration often renders useless an activation of an implant by exposing the implant to plasma at the implant's manufacturing site, because it may not be possible to ensure using the implant within a short period of time after the exposure to plasma, so as to retain the benefits of such exposure. It would therefore be advantageous to provide for plasma treating an implant in a medical care center, soon before a medical procedure for installing the implant is carried out. Additionally or alternatively, the implant may be plasma-treated a long time (e.g.—more than a day) before the medical procedure, and then be stored until the medical procedure in such environment and conditions that retain the beneficial effects of the plasma treatment. Such environment and conditions may include storing the implant in a polar liquid, possibly saline, for the period between the plasma treatment and the medical procedure.

It would also be advantageous to carry out such a plasma treatment prior to implantation in sterile conditions. One reason is that the plasma treatment according to the teachings herein should not, preferably, be followed by a sterilization process, because such a sterilization process would likely ruin the beneficial effects of the plasma treatment. In other words, a preferred sequence of steps according to the teachings herein should include providing an implant which is sterilized, and plasma-treating the implant in sterile conditions prior to implantation. Thus the implant which is being provided sterile to the plasma treatment, may remain sterile during the plasma treatment and following the plasma treatment, hence being substantially immediately ready for implantation following the plasma treatment.

Characteristics of the electric field that could generate plasma in a fluid, may depend strongly on characteristics of the fluid itself, in addition to the geometry involved (such as shape and configuration of electrodes used for the application of the electric filed, distance between the electrodes etc.). Generally, if the fluid is a gas, the higher the pressure of the gas, the higher the electric field should be to ignite plasma. Also, some gases ignite at lower fields than others. For example, helium gas at atmospheric pressure ignites at an RF field (in a frequency between 1 MHz and 15 MHz) of about 7 KV over a distance of 1 cm between (plate) electrodes, and at a voltage of about 200V in 0.8 KPa with the same electrodes configuration. With a similar configuration of electrodes and at similar field frequencies, air ignites at a voltage of about 20 KV in atmospheric pressure and at a voltage of about 800V in 0.8 KPa.

The characteristics of the electric field that could generate plasma also depend on the mode of plasma generation. For example, according to some preferred embodiments, plasma in a vicinity of a dielectric implant such as a breast implant may be generated in a Dielectric Breakdown Discharge (DBD) mode. According to some particular variations of a DBD mode of operation, the field may be generated between two electrodes, whereas the dielectric implant is positioned in between the electrodes. Furthermore, in some such embodiments the dielectric implant is the only dielectric object positioned in the line of sight between the electrodes. FIG. 12 in Application '326 and FIG. 10 in Application '396 disclose various embodiments of devices configured to provide plasma treatment to a breast implant, and some related electrodes configurations. Plasma may typically be generated in these devices by applying high voltage (HV) between at least a pair of electrodes, e.g. one beneath the implant and one above the implant, so that the implant is in between the electrodes. It was found that in such configurations, glow discharge appears along flickering and swaying plasma filaments that extend from the electrode substantially towards the implant. The plasma filaments continue and spread over the implant's surface in all directions until fading away at some distance from the electrode, defining a spatial area which is effectively treated.

Although a single electrode (and even a pointed electrode, as disclosed for example in '396) generates glow discharge and plasma over a relatively large area of a breast implant, the intensity of glow discharge is not uniform over that area, possibly indicating non-uniform electric current density passing therethrough. In other words, regions of the implant closest to the electrode may experience a higher electric current density and a more intense plasma treatment (e.g. the intensity of surface activation), demonstrated by a more intense glow discharge; and regions that are more distant from the electrode might experience a lower electric current density, and a less intense plasma treatment, demonstrated by a less intense glow discharge. Such a non-uniform treatment is less than optimal.

There is thus provided according to an aspect of the invention a method for treating a dielectric implant prior to using the implant in a medical procedure. The method comprises applying a plasma-generating electromagnetic (EM) field using at least one electrode so as to generate plasma in a vicinity of the implant while displacing the electrode and the implant relative to one another. According to some embodiments the plasma treatment is applied in a medical center just prior or soon prior to the medical procedure.

According to some embodiments the plasma treatment according to the teachings herein is carried out a relatively long time—typically more than a day—before the medical procedure, and the implant is stored in a polar liquid, possibly saline, following the treatment and until the medical procedure.

There is provided according to a further aspect of the invention a portable plasma module for treating an implant prior to using the implant in a medical procedure. The plasma generating module comprises a structure and at least one electrode fixed to the structure and configured to apply a plasma-generating electromagnetic (EM) field for generating plasma in a vicinity thereof. The plasma generating module further comprises a table configured to support the implant, being mechanically associated with the structure so as to enable the table and the structure to constrictively displace relative to one another ("constrictive displacement" herein means a displacement along pre-defined constricted trajectories, for example a circular trajectory). The plasma generating module further comprises a module mechanical connector configured to connect the portable plasma module to a transmission unit associated with a motor, to allow displacing the table and the structure relative to one another. And the plasma generating module further comprises a module HV electrical connector configured to associate an EM power source to the at least one electrode to apply the plasma-generating electromagnetic (EM) field by the electrode.

According to a further aspect of the invention, there is provided a docking station configured to connect to a portable plasma module to enable generation of plasma therein, thereby forming together a plasma generation system. The docking station may comprise a high voltage (HV) power source and a station HV electrical connector electrically associated with the HV power source and configured to connect to an electrical connector of the portable plasma module, thereby electrically associating at least one electrode of the portable plasma module with the HV power source. The docking station may further comprise a transmission system mechanically associated with a motor, and a station mechanical connector, configured to connect to a module mechanical connector of the portable plasma module, thereby enabling mechanically associating the transmission system with a displaceable member of the portable plasma module.

There is further provided according to an aspect of the invention, a plasma generating apparatus for treating an implant prior to using the implant in a medical procedure. The plasma generating apparatus comprises a structure and at least one electrode fixed to the structure and configured to apply a plasma-generating electromagnetic (EM) field for generating plasma in vicinity thereof. The plasma generating apparatus further comprises a high voltage (HV) power source, electrically associated with the electrode. The plasma generating apparatus further comprises a table configured to support the implant. The table is mechanically associated with the structure so as to enable the table and the structure to constrictively displace relative to one another. The plasma generating apparatus further comprises a motor mechanically associated with the structure and with the table, being thereby configured to displace the structure and the table one relative to the other. The plasma generating apparatus further comprises a control unit functionally associated with the HV power soured and with the motor. The control unit is configured to control the operation of the HV power source and the motor. The plasma generating apparatus further comprises an operation panel electrically associated with the control unit and enabling an operator commanding the plasma treatment apparatus.

It is noted that a non-uniform plasma application over the implant's surface might result in a risk of either being only partially effective (namely leaving portions of the implant untreated), or being too intense (possibly damaging portions of the implant due to exposure to too high accumulated energy). By displacing the implant and the electrode that applies the plasma-generating EM field relative to one another, various regions of the implant's surface move closer and further away, periodically or intermittently, to and from the electrode. Accordingly, regions of the implant's surface—preferably most or all of the implant's surface—are subjected to an electric current that periodically or intermittently increases and decreases. Compared to configurations in which the implant and the electrode are fixed relative to one another, the integrated current over the treatment duration in various regions of the implant's surface is hence more uniform, and as a result, the plasma treatment intensity and effectiveness are more uniform.

Certain embodiments of the present invention may include some, all, or none of the above advantages. Further advantages may be readily apparent to those skilled in the art from the figures, descriptions, and claims included herein. Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 1A schematically depicts an embodiment of a plasma generating apparatus for treating a breast implant prior to using the implant in a medical procedure;

FIG. 1B schematically depicts an embodiment of an electrode of the plasma generating apparatus of FIG. 1A;

DETAILED DESCRIPTION OF SOME EMBODIMENTS

The principles, uses and implementations of the teachings herein may be better understood with reference to the accompanying description and figures. Upon perusal of the description and figures present herein, one skilled in the art is able to implement the teachings herein without undue effort or experimentation.

Figure 1C:
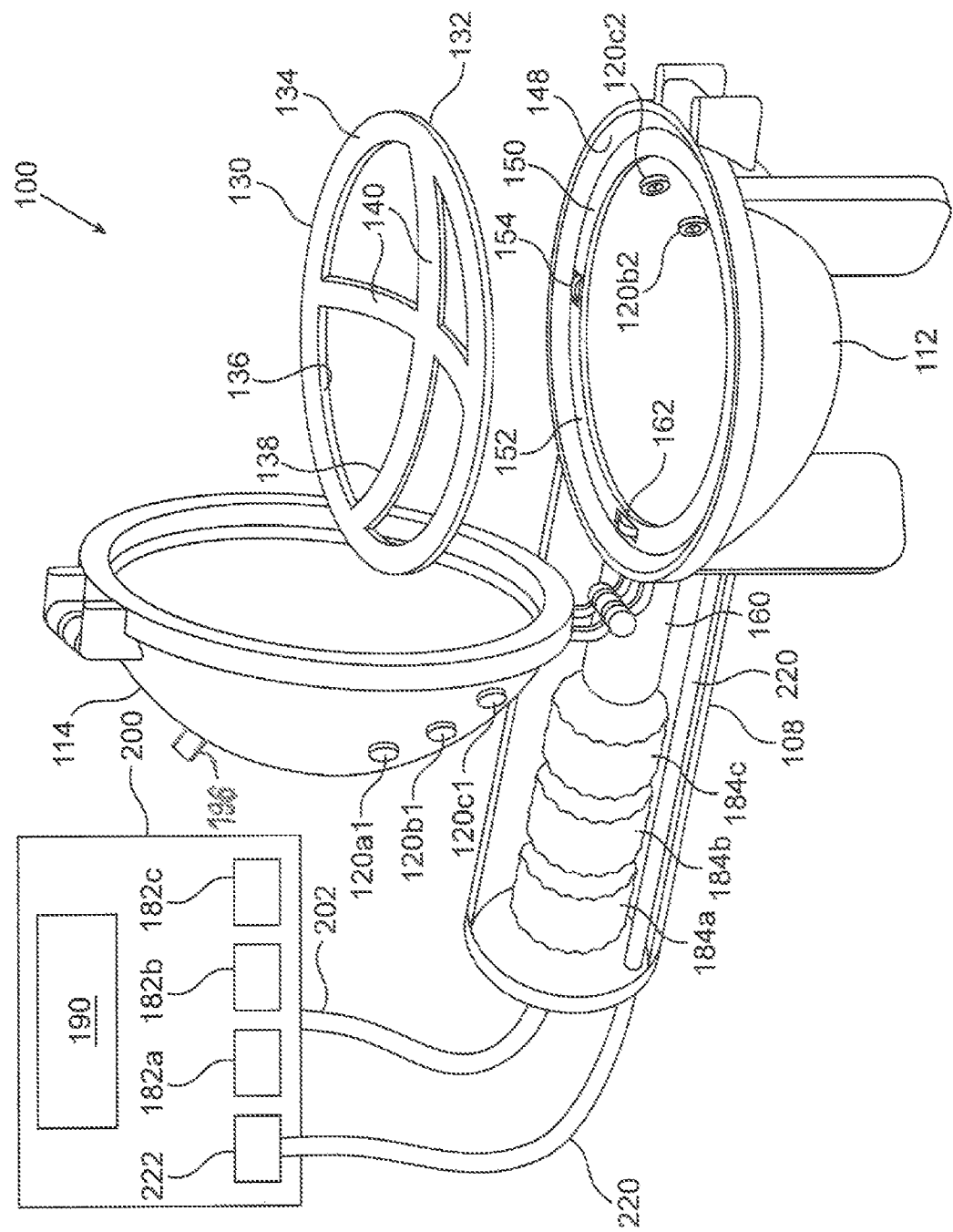
FIG. 1C schematically depicts, in a partially-exploded view, the plasma generating apparatus of FIG. 1A with the plasma chamber being open.

FIG. 1A schematically depicts an embodiment of a plasma generating apparatus 100 for treating a breast implant prior to using the implant in a medical procedure. Plasma generating apparatus 100 comprises an auxiliary unit 108 and a plasma chamber 110, depicted here in a closed configuration. The auxiliary unit is described in more detail in FIG. 1C. Plasma chamber 110 comprises a base 112, and a cover 114 configured to lock onto base 112, both made of a dielectric material such as glass or a polymer. At least one of base 112 and cover 114 is concave, possibly curved, so as to define an internal void (not explicitly shown here) inside the plasma chamber when cover 114 is locked onto base 112. The internal void is advantageously shaped roughly as an ellipsoid, being dimensioned and configured to house a breast implant in the plasma chamber, however other shapes such as a box are also contemplated. According to some embodiments, a size of the inner void of plasma chamber 110 is preferably selected and suited for treating a breast implant of a given size, hence breast implants of different sizes may preferably be treated in plasma chambers 110 of different sizes. According to some embodiments, the void inside plasma chamber 110 is sealed from the ambient when cover 114 is locked onto base 112. According to some embodiments the plasma chamber is closed during operation, but not sealed.

Plasma chamber 110 comprises one or more pairs of electrodes 120 (denoted here electrode pairs 120a, 120b and 120c), each electrode pair being configured to apply a plasma-generating electromagnetic (EM) field inside the plasma chamber, when supplied with a suitable voltage between the electrodes of the pair, and even when an implant to be treated is dispose inside the plasma chamber, substantially in between the electrodes of the pair. Each electrode pair 120 comprises two electrodes positioned distantly from one another, preferably opposite to one another relative to the internal void of the plasma chamber. Specifically, plasma chamber 110 comprises electrodes 120a1, 120b1 and 120c1 positioned on cover 114 and three corresponding electrodes (not shown here) positioned on base 112.

Plasma generating apparatus 100 further comprises an operation unit 200, connected with a cable 202 to the auxiliary unit 108. Operation unit 200 comprises an operation panel 210, the operation unit being configured to enable a user command the plasma generating apparatus through the operation panel, and to obtain operational data therethrough.

FIG. 1B schematically depicts one of the electrodes in the plasma chamber 110 (such as, for example, electrode 120a1)

in an enlarged view. Electrode 120a1 is shaped as an elongated narrow spike 122 passing through the wall (base 112 or cover 114) of the plasma chamber, i.e. having an external end thereof outside the plasma chamber and an internal end thereof inside the plasma chamber. A HV insulated cable 124, advantageously located externally to the plasma chamber, electrically associates the electrode with a HV power source (not shown here). The HV cable 124 is advantageously external to the plasma chamber to minimize the risk of plasma generation inside the chamber by the field generated by the conductor of the cable, and to minimize mutual influence on the plasma-generating field of any one electrode, by the conductors to the other electrodes. The internal end of the electrode may protrude into the void of the plasma chamber from the wall (base or cover) and may be shaped to be pointed, thereby producing a higher field at a given voltage supplied to the electrode. The electrode may be surrounded by an electrode sleeve 126 protruding from the internal surface of the plasma chamber's wall and having an open end 128, to prevent contact of the breast implant with the electrode and thus preventing damage to the implant.

FIG. 1C schematically depicts, in a partially-exploded view, plasma generating apparatus 100 with plasma chamber 110 being open. Plasma chamber 110 comprises a table 130 detached from base 112 and from cover 114 or at least movable relative thereto. Table 130 comprises a frame 132 shaped as a planar ring 134 defining an inner circle 136, and an implant support 138, fixed to the frame and shaped as a cross 140 over the area bounded by the inner circle 136 of the ring. Implant support 138 is configured to support a breast implant disposed thereon, leaving exposed as large portion as possible of the implant's bottom surface. Thus table 130 is advantageously dimensioned so that the ring inner circle 136 is larger than the breast implant's diameter (when the implant is disposed on table 130), and consequently no portion of the implant may be hidden from the plasma by being in contact with the ring. Further, the arms of cross 140 are thin as possible, to hide as small portion as possible from the implant's bottom surface. The table may thus be characterized by a support aspect ratio defined as the ratio between the net area of the table (the area of the top view of the ring 134 and the cross 140 in this particular embodiment) to the area bounded by the external boundary of the table.

Plasma chamber 110 further comprises a table support 150, configured to support table 130 thereon while allowing table 130 to move relative to plasma chamber 110. Table support 150 comprises a horizontal ring 152 fixed to base 112 below a rim 148 of the base. Table support 150 further comprises three or more wheels 154, positioned along horizontal ring 152, being protruding upwards from horizontal ring 152 and rotatable about radially aligned axes. During operation table 130 is positioned on table support 150 supported by wheels 154, being thereby able to revolve around the center of the circle 136 and restricted from displacing sidewise by rim 148.

Plasma generating apparatus 100 further comprises a motor 160, external to plasma chamber 110, for revolving table 130 during the generation of plasma inside plasma chamber 110. A motor shaft (not shown here) of motor 160 is mechanically associated, possibly via a transmission unit (not shown here), e.g. a gear system, to a driving wheel 162, thereby effecting a rotation of wheel 162 when motor 160 rotates. Driving wheel 162 is located inside plasma chamber 110, being configured to revolve table 130 around the center of circle 136 as described above, when being rotated by motor 160. Specifically, driving wheel is protruding upwards from horizontal ring 152, being rotatable about a radially aligned axis. Thus, when table 130, with a breast implant placed thereon, is positioned on table support 150, driving wheel 162 may engage with planar ring 134, e.g. by friction, to effect a revolution motion about a vertical axis of the table support when driving wheel 162 rotates. Other methods of mechanical association between motor 160 and table 130 are contemplated, particularly other methods of engagement between the driving wheel and the table. For example, such engagement may utilize a cogged driving wheel and a corresponding cogged bottom surface of planar ring 134. According to some embodiments motor 160 is encased in auxiliary unit 108, the auxiliary unit being attached to the plasma chamber.

Plasma generating apparatus 100 further comprises one or more high-voltage (HV) power sources (depicted explicitly in FIG. 2), each power source comprising an RF generator 182 and a step-up transformer 184. RF generators 182 may conveniently reside in the operation unit 200, and cable 202 is employed to electrically connect the operation unit 200 (and components therein, such as the signal generators) to the auxiliary unit 108 (i.e. the components therein). Specifically, in the embodiment schematically depicted in FIG. 1C, three RF generators denoted 182a, 182b and 182c, are individually electrically associated with three step-up transformers 184a, 184b and 184c, respectively. In the HV power source, low voltage, high current, radio frequency (RF) signal is generated in the RF generator and supplied to the step-up transformer which produces a corresponding RF high voltage signal, typically above 1 KV.

The step-up transformers 184 are each electrically associated with each pair of electrodes 120 of the plasma chamber. Typically, such electrical association may simply comprise electrical connection, however capacitive coupling or inductive coupling may also be employed and "electrically associated" is inclusive herein of capacitively or inductively coupled. Particularly, in embodiments wherein the table and implant are stationary relative to the chamber and the electrode or electrodes are displaceable, non-wired electrical associated between the power source and the electrodes—e.g. capacitive coupling—may be preferred The voltage produced by step-up transformer 184a is applied inside the plasma chamber between electrode 120a1 in the cover and a corresponding electrode (not shown here) in the base 112. Likewise, the voltage produced by step-up transformer 184b is applied inside the plasma chamber between electrode 120b1 in the cover and electrode 120b2 in the base, and the output voltage of step-up transformer 184c is applied between electrode 120c1 and electrode 120c2. According to some embodiments the step up transformers 184 may advantageously be located close (but externally) to the plasma chamber e.g. in the auxiliary unit 108, so as to minimize the length of conductors (HV cables) between the step-up transformers and the associated electrodes.

Figure 2:
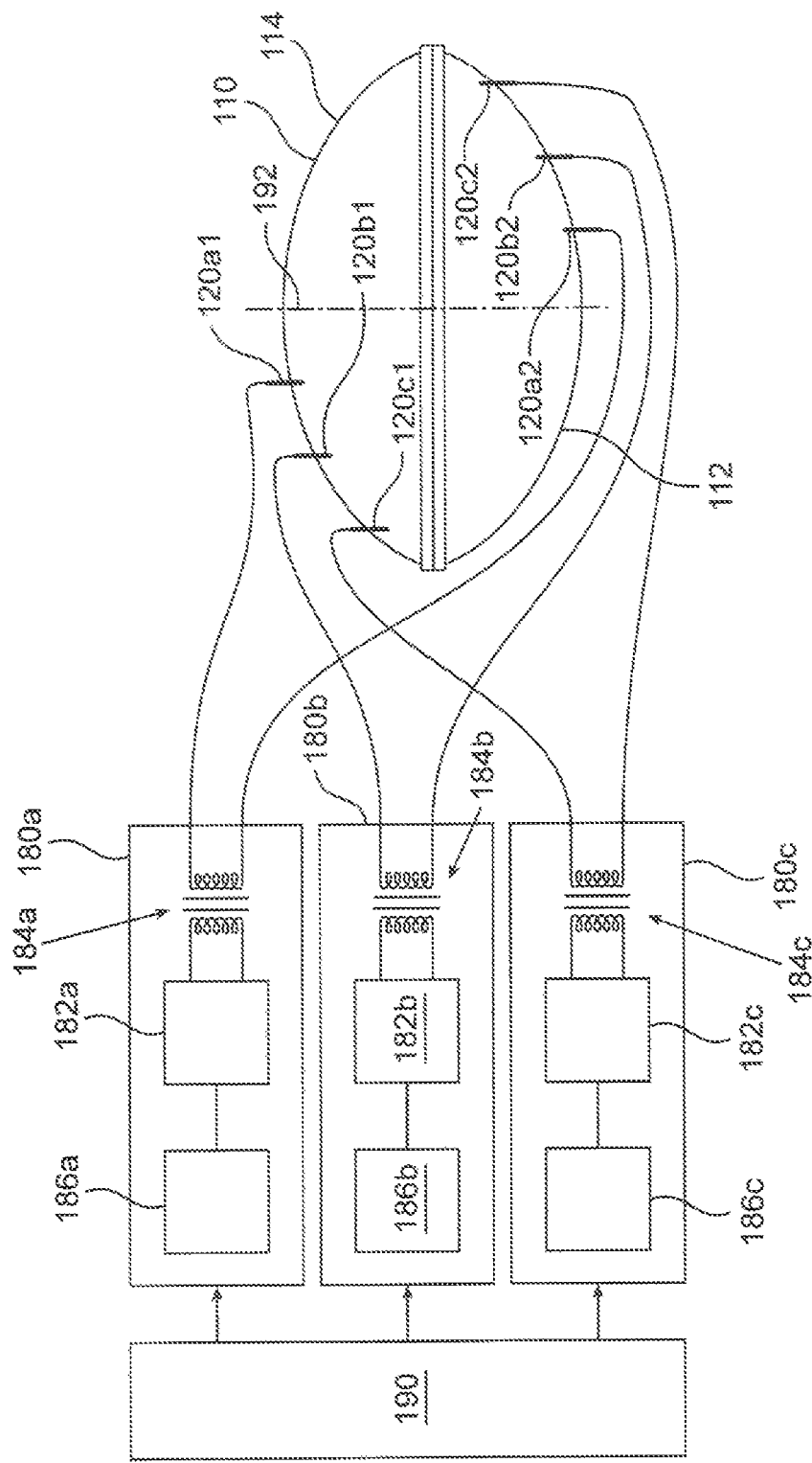
FIG. 2 schematically depicts an embodiment of an electronic circuitry of the plasma generating apparatus of FIG. 1A.

FIG. 2 schematically depicts an embodiment of an electronic circuitry of the plasma generating apparatus 100. Each electrodes pair 120 is electrically associated with a respective HV power source 180 (specifically electrodes pair 120a with HV power source 180a etc.). Each HV power source 180 comprises RF generator 182 which is electrically associated with the respective step-up transformer 184 as described above. Each RF generator is configured to generate a continuous or modulated RF signal of a controlled high (radio) frequency. In a modulated RF signal, the modulation is determined by a signal generator 186, associated, exclusively and respectively, with each RF generator

182. For example, signal generator 186*a* is electrically associated with RF generator 182*a* and controls the RF modulation thereof; and so on. According to some preferred embodiments, the RF generators produce pulsed RF signals, and the signal generators 186 correspondingly determine the pulse width (PW) and repetition rate or pulse frequency (PRF) of the RF signal. A control unit 190 is electrically associated with the HV power sources 186, allowing to control the operation thereof, namely to select operational parameters such as PW, PRF and overall duration of applying the HV power. Each electrodes pair may receive a different RF signal as is further explained below. Further, the RF signals to the different electrodes pairs may be synchronized so that when one electrodes pair receives a pulse, the signals to the other two pairs are in off ("no pulse") period of the pulse modulation.

According to some embodiments, the electrodes of electrodes pairs 120 are distributed on the cover 114 and the base 112 so that during operation, when the table revolves with the breast implant thereon, surfaces of different areas of the implant are covered by the different electrodes pairs. The table with the implant revolves around an axis of rotation 192, hence, the more distant an electrode is from the axis 192, the greater is the area which is exposed to the plasma generated by that electrode. For example, the electrodes of electrodes pair 120*c* are located farthest away from axis 192, hence, as the implant revolves around the axis, the area of the implant's surface exposed to the plasma generated by these electrodes, is the largest. And the electrodes of electrodes pair 120*a* are located closest to axis 192, hence, as the implant revolves, the area of the implant's surface exposed to the plasma generated by those electrodes, is the smallest. Hence, according to some embodiments, some parameters of the high voltage delivered to the electrodes may vary from one electrodes pair to another. In other words, the plasma-generating EM field produced by electrodes pair 120*a* may be less intense and/or shorter in duration or less energetic compared to, e.g., the plasma-generating EM field produced by electrodes pair 120*c*, so that the averaged areal density of energy supplied by each pair of electrodes on the implant's surface is roughly the same.

According to some embodiments, the RF HV supplied to the electrodes may be pulsed, and the duty cycle of the pulses may vary according to the electrodes pair being used. According to some exemplary embodiments, signal generators 186 may be configured to generate a pulsed signal for modulating the RF generators 182, the PRF of which is selected in the range of 10 Hz-10 KHz, and more preferably between about 100 Hz and about 5 KHz. The PW of the pulsed signal may be selected in the range between 0.1 μsec (microsecond) and 10 msec (milliseconds), and more preferably larger than 1 μsec. More generally, when the PW and PRF of a pulsed signal is concerned, such parameters may be selected in accordance with other operational parameters of the plasma generating apparatus, e.g. the frequency of the HV signal supplied to the electrodes. For example, the PW is preferably selected so as to include in a single pulse duration more than several (e.g. 3, or 5) cycle periods of the carrier RF HV signal. Hence, if the frequency of the HV signal is 1 MHz, then the PW is preferably selected to be larger than 5 μsec, so as to encompass about 5 cycle periods of the HV signal in a single pulse. The PPF may then be selected to be about 0.5-2 KHz, yielding a duty cycle of about 0.25%—1%. With the same field frequency of 1 MHz, the pulse width may be selected in a range of up to 100 μsec or 200 μsec, if the PRF is 2 KHz, or even up to 1 msec if the PRF is about 0.5 KHz, yielding in this last example a duty cycle of about 50%.

According to some embodiments, some parameters of the HV signal supplied to the electrodes may be different between the electrode pairs as discussed above, to ensure uniform areal density of plasma energy applied to the implant's surface. According to some embodiments, different electrodes pairs may be supplied with HV signals with different duty cycles. In other words, the duty cycle of the signals delivered by signal generators 186*a*, 186*b* and 186*c* may be different from one another, so as to compensate for the different surface areas the corresponding electrodes cover. Thus, electrodes pair 120*a* may be supplied with a HV signal with a relatively low duty cycle, electrodes pair 120*b* with a medium duty cycle and electrodes pair 120*c* with a relatively high duty cycle. It should be understood to the person skilled in the art, that other methods, and other parameters of the electronic circuitry of the plasma generating apparatus may be selectively controlled to obtain the result of a uniform areal energy density of the plasma on the implant's surface. Such other parameters may include different field intensity (as applied by the electrodes), different HV amplitude (as supplied to the electrodes), and various combinations of some or all of the above.

By associating each electrodes pair 120 with an exclusive power source 180, two or more of the electrodes pairs may apply plasma-generating EM fields in the plasma chamber independently from one another, namely simultaneously, or during partly-overlapping time sequences or during non-overlapping time windows. In other words, if a single power source such as power source 180 is directly connected to several (two or more) electrodes pairs in parallel, all the electrodes pairs must be activated together, being supplied from the same power source. This may be less than optimal, because different electrodes pairs may not be supplied with different RF signals, hence maintaining uniform activation of the implant's surface may be more difficult to achieve. Moreover, mutual interactions between the fields generated by the electrodes in such a case might affect destructively the uniformity or the intensity of the fields, or both. Additionally or alternatively, a single power source may be used with several electrodes pairs, using, e.g., a HV distributor, namely a HV switch that may be configured and operable to sequentially connect the power source to each of the electrodes pairs. Some embodiments of this method however might result in a longer overall treatment time, as employment of the electrodes pairs is sequential and not simultaneous.

Yet other methods are contemplated. According to some embodiments, one or more of the electrodes may be dynamically displaced relative to the walls of the plasma chamber during operation. For example, a single pair of electrodes may be used, one located on the cover and the other on the base. During operation, as the table with the implant is rotated, the electrodes may be displaced radially, maintaining a mutually opposite position relative to the center of the plasma chamber, from near the axis 192 region to the periphery of the base (or cover). By so moving back and forth along the radial direction, a single pair of electrodes may apply plasma to the entire surface of the implant. It should be understood by the person skilled in the art that using a single pair of electrodes according to the method described hereinabove may require more time to complete plasma treatment, compared to using several pairs of electrodes simultaneously.

Other methods are further contemplated. According to some embodiments, more than 3 electrodes pairs may be used to apply the plasma in plasma chamber 110. According to some embodiments, as many as 5 or 10 or even more than 10 electrodes pairs may be employed, some or all being arranged at different radial distances from the rotation axis 192. The electrodes pairs may be arranged at relatively small radial distances from one other thereby affecting a higher uniformity of the energy distribution over the implant's surface. Furthermore, more than one electrodes pair may be associated with one radial distance from the rotation axis, to compensate for the larger areas of concentric stripes at larger radii from the axis. A combination of a different number of electrodes at different radii, and different average power supplied to the electrodes at different radii, may be employed to optimize energy distribution uniformity.

According to some embodiments the electrodes may be shaped differently from the pointed tip depicted in FIG. 1B. According to tome embodiments at least some electrodes may be shaped as stripes oriented radially or tangentially or in any other direction. According to some embodiments the stripes may follow a section of a spiral. According to some embodiments at least some of the electrodes may be assume a two-dimensional shape on the wall (cover 114 or base 112) of the plasma chamber 110. According to some embodiments each electrode may be shaped as a circle or a triangle or a quadrilateral etc.

According to some embodiments a piezoelectric element may be used as a HV transformer, for directly transforming a RF, low-voltage signal to a RF, plasma-generating EM field. Suitable piezoelectric elements may be commercially provided, for example, by Nihon Ceratec Co. Ltd. (http://www.ceratecinc.com/pdf/transformer/Piezoelectric Transformer_InverterModule.pdf), and by EPCOS AG (https://en.tdk.eu/tdk-en/373562/tech-library/articles/applications---cases/applications---cases/cold-plasma-from-a-single-component/1109546).

Typically, such a piezoelectric element may be configured and operable to transform a RF, low-voltage signal, supplied to a low-voltage portion of the piezoelectric element, to a RF, high-voltage signal, which is generated at a high-voltage end of the element. Thus, according to some embodiments, each piezoelectric element may be arranged in the plasma chamber 110, so that the high-voltage end of the thereof is inside the chamber whereas the low-voltage portion may conveniently be located outside the chamber. In other words, the piezoelectric element may be arranged so as to sealingly pass through the cover 114 or the base 112, in locations suitable for the generation of the plasma-generating EM field. It is noted that in such embodiments a single piezoelectric element may function as electrodes pair such, for example, electrodes pair 120a of FIGS. 1A-1C. According to some embodiments the piezoelectric elements may be arranged on the cover (as described for example for electrodes 120a1-120c1), whereas reference electrodes, electrically associated with the ground potential of the driving circuitry, may be arranged in the base (as described for example for electrodes 120a2-120c2).

Reverting to FIGS. 1A and 1C, according to some embodiments, plasma generating apparatus 100 may further include a fluid channel 220 such as a gas tube, fluidly associating the inner void of plasma chamber 110 with a gas pump 222 or a gas reservoir (not shown in these Figures) outside the plasma chamber. According to some embodiments plasma may be generated in the plasma chamber in non-ambient atmosphere, hence, following inserting the implant to the plasma chamber and closing the chamber, the atmosphere within may be changed. According to some embodiments pump 222 may be used to pump air from the plasma chamber, for applying the plasma in a low-pressure air-based atmosphere. The pump may be housed in the operation unit 200, the fluid channel 220 being possibly attached to cable 202 for fluidly connecting the pump with the plasma chamber. Alternatively the pump may reside in the auxiliary unit and commanded from the operation unit 200. It should be noted however that some commercialized breast implants have compressible portions made of porous or sponge-like materials in their interior. Such breast implants if exposed to low pressure atmosphere may suffer destructive swelling. Plasma treatment at about atmospheric pressure is therefore advantageous in such breast implants.

According to some embodiments the plasma may be generated in the plasma chamber with an atmosphere which is not air. For example, the plasma chamber may be, flushed with another gas (e.g. Argon) possibly following, or simultaneously with pumping of air from the chamber. Accordingly, the plasma generating apparatus may be fluidly associated to a suitable gas reservoir (e.g. a pressurized gas tank). According to some embodiments the gas reservoir may be associated with the plasma chamber via the fluid channel 220, or, alternatively, through another tube (not depicted here). According to some embodiments the plasma chamber may be filled with the other gas up to a pressure lower than atmosphere (e.g. below about 0.01 Atm., or below about 0.1 Atm.). In some of such embodiments the plasma chamber is configured to be sealed when closed, so that air cannot penetrate to mix with the gas inside the plasma chamber.

According to some embodiments plasma may be generated in a non-air atmosphere at a pressure higher than atmospheric pressure. In such embodiments the plasma chamber may be flushed with the other gas, with or without the prior pumping of the air from the chamber. If air is not pumped from the chamber, the plasma chamber may be closed but not sealed, whereas after closure (and also during the plasma treatment) the chamber may be being continuously flushed with the other gas. The excess pressure inside the plasma chamber may generate in such embodiments an outflow of gas therefrom, thereby providing after a short period of flushing (e.g. a few second, e.g. 10 sec or 30 sec or 1 min or a few minutes) an atmosphere dominated by the other gas inside the chamber, allowing plasma generation. The rate of flow of gas into the chamber may be adapted to the leakage from the plasma chamber outwards, so as to maintain the atmosphere inside the chamber within a desired range of pressure, e.g. above about 1.01 Atm or above about 1.1 Atm., or above about 1.2 Atm. The Plasma generating apparatus may include a pressure gauge for measuring the pressure inside the plasma chamber, thereby ensuring that the plasma treatment is within the desired process parameters and is not compromised due to, e.g., gas pipe blockage or too high pressure.

According to some embodiments, the silicone implant may be wetted by a liquid—possibly a polar liquid such as an aqueous solution or aqueous suspension, or immersed in such a liquid, following the plasma treatment. Following the plasma treatment the liquid may tend to wet the implant's surface thereby forming liquid layer on the entire surface of the implant or at least on the major portion of the surface. Such wetting may be typically more pronounced for polar liquids such as water, but is not limited thereto. According to some embodiments, the liquid may include medically effective agents which may adhere, at least temporarily, to the implant following such wetting, and generate a medical effect in the patient's body following implantation. According to some embodiments the medically effective agent is selected from the group consisting of antimicrobial agents, anesthetics, analgesics, anti-inflammatory agents, anti-scarring agents, anti-fibrotic agents, anti-cancer compounds, hemostatic material for controlling bleeding, hormone therapeutics, stem cells, and cellular precursors. According to some embodiments the at least one medically effective agent is an antimicrobial agent selected from the group consisting of antibiotics, antiseptics, and disinfectants. According to some embodiments the at least one medically effective agent is an antibiotic selected from the group consisting of cefamizine, gentamicin, vancomycin, rifampin, minocycline and cloxacillin.

According to some embodiments the wetting of the implant by the liquid—possibly the polar liquid—as discussed above, may be done following the plasma treatment when the implant is still inside the chamber 110. According to some embodiments, plasma chamber 110 may thus comprise at least one liquid input port 196 for injecting the liquid into the chamber following the plasma treatment. The liquid may be sprayed onto the implant, and two or more liquid input port 196 may be employed to ensure full coverage of the implant's surface by the spray. According to some embodiments such spraying may be done during the continuing revolution of the implant in the chamber, on table 130, to increase uniformity of the spread of liquid on the implant.

According to some embodiments the implant may be immersed in the liquid inside the chamber, by injecting the liquid to the chamber until the implant is fully immersed therein. The liquid input port 196 may be equipped with a liquid valve (not shown here) that may be used to close and seal the port during plasma activation and to open the port for liquid passage during implant wetting. If plasma is generated in the chamber under vacuum, it may suffice to connect the liquid input port to the liquid source so that, following opening the liquid valve, the liquid may be sucked into the chamber due to the atmospheric pressure outside the chamber. If the plasma is activated at atmospheric pressure, then the liquid must be pressurized into the chamber, while the gas in the chamber is pressed out of the chamber, possibly through a leak aperture or a unidirectional valve (not shown here).

According to some embodiments operation unit 200 comprises control unit 190 configured to control some operations of the plasma generation apparatus. Control unit 190 is electrically associated with operation panel 210, being configured to process user commands received from the operation panel, into commands to various units, components and modules of the plasma generating apparatus. Control unit 190 is further configured to receive signals from such units, components and modules—e.g. sensors of the apparatus—and process such signals to indications provided to a user on the operation panel or to automatically executed operations. According to some embodiments control unit 190 may comprise a digital processor (not shown in these Figures) capable of executing software codes.

An exemplary use of the plasma generating apparatus may thus include according to some embodiments a step of providing by a user operational parameters for a session of plasma treatment by using the operation panel. Such operational parameters may include, for example, duration of the plasma treatment, field intensity (namely amplitude of voltage provided to the electrodes), EM field frequency, table rotation speed, pulse parameters—PW and PRF—of the signal modulation and so on. Additionally or alternatively, the user may select, from a pre-programmed list, using the operation panel, a type of a breast implant that is to be plasma treated, and according to such selection a set of pre-programmed operational parameters may be obtained from the control unit to command the units' components and modules of the apparatus.

According to some embodiments plasma chamber 110 may be equipped with an open/closed sensor such as a micro-switch, configured to provide indication on whether the plasma chamber is open or closed. According to some embodiments the plasma generating apparatus may include a gas flow meter for measuring the flow rate of a gas from a gas reservoir into the plasma chamber during flushing. According to some embodiments a revolution speed meter in the plasma chamber may be used to measure the table's rotation speed. According to some embodiments the plasma chamber may include an optical sensor configured to detect the glow associated with plasma generation for indicating plasma ignition and continuous generation in the chamber. All or some of the above described sensors and components may be electrically associated with the control unit 190, the control unit being configured to use data received from such components or to provide such data to a user. For example, the control unit may be programmed to enable HV supply to the electrodes (and the consequent plasma generation) only if the open/closed sensor indicates a closed plasma chamber, the revolution speed meter indicates that the table revolves and if the flow meter and the pressure gauge indicate flow rate and pressure in the plasma chamber, respectively, within their predetermined ranges.

Figure 3A:
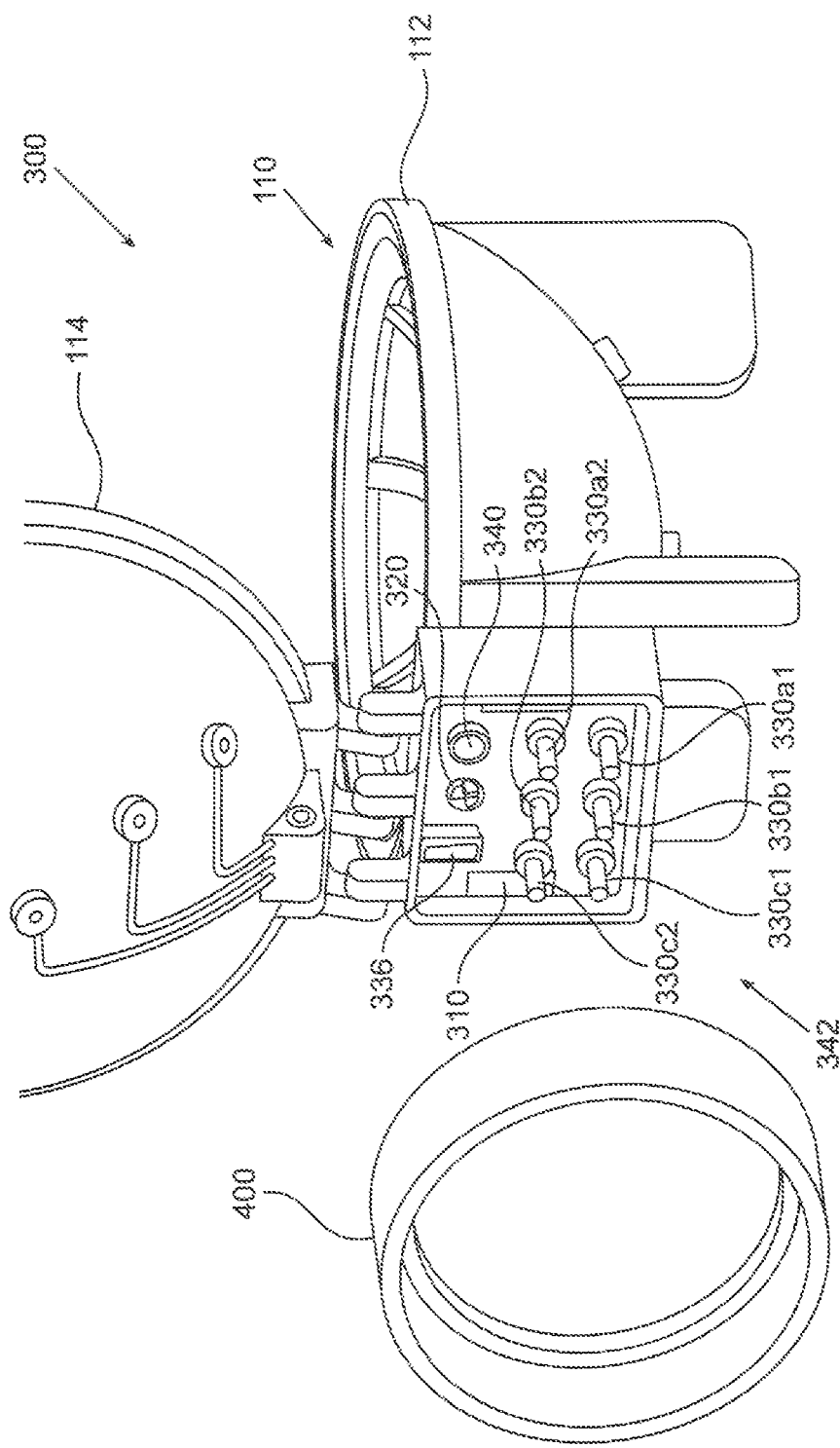
FIG. 3A schematically depicts an embodiment of a portable plasma module according to the teachings herein in a semi-exploded view, and FIG. 3B schematically depicts an embodiment of a docking station configured to connect to the portable plasma module of FIG. 3A.
Figure 3B:
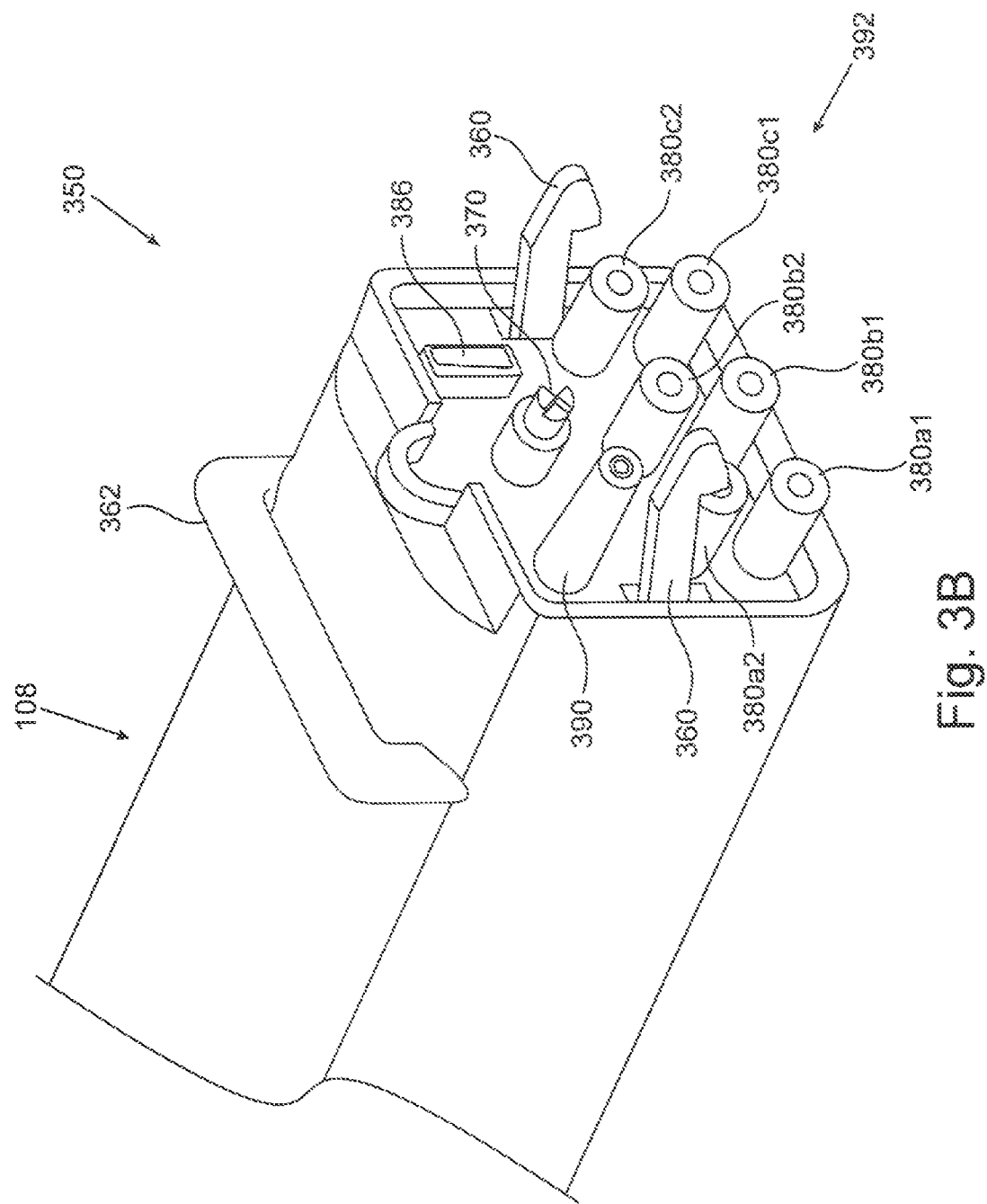

FIGS. 3A and 3B depict two components of a plasma generating system. FIG. 3A depicts an embodiment of a portable plasma module 300 in a semi-exploded view. Portable plasma module 300 comprises plasma chamber 110 described above. FIG. 3B schematically depicts an embodiment of a docking station 350 which comprises auxiliary unit 108 and may be connected to an operation unit (not shown in these Figures) such as, for example, operation unit 200. Docking station 350 is configured to connect to portable plasma module 300 to form together (being also connected to the operation unit) the plasma generating system. According to some embodiments the plasma generating system may be used for plasma treating a breast implant prior to installing the implant in a medical procedure in a medical care center (such as a hospital or a clinic). According to some embodiments docking station 350 may be permanently situated at the medical care center whereas the portable plasma module 300 may be used only once, namely for providing plasma treatment to a single implant only. According to some embodiments the breast implant may be shipped to the medical care center encapsulated in portable plasma module 300. According to some embodiments the implant and the portable plasma module may be shipped to the medical care center separately, and the implant may be placed in the portable plasma module for plasma treatment, just prior to the implantation of the implant. According to some embodiments, the portable plasma module is maintained sterile throughout the process so that a sterile implant may be plasma-treated in the plasma generating system, and remain sterile for implantation. According to some such embodiments, the docking station 350 may not necessarily be sterile.

Additionally or alternatively, the plasma generating system may be used to plasma-treat an implant a relatively long time (e.g., more than a day) before the implantation, e.g. at the manufacturing site. According to some such embodiments, the portable plasma module may be filled with a polar liquid—e.g. saline—after the plasma treatment. The implant may be stored immersed in the liquid for a long time, and may further be shipped or transported, stored within the portable plasma module. The implant may be so transported e.g. to a medical care center where an implantation is expected to be carried out, and be removed from the portable plasma module shortly before the operation.

Docking station 350 comprises a station connector 360 in a form of a hook, configured to connect to a corresponding module connector (310 in FIG. 3A) in the portable plasma module 300, thereby attaching portable plasma module 300 to docking station 350. A "module connector" here refers to a male or a female portion of connector, or a socket or a plug, corresponding to a female or male portion, or a plug or a socket, respectively, in a corresponding "station connector", configured to connect with the module connector. Docking station 350 further comprises a release handle 362 configured to release the connection between station connector 360 and the module connector by pressing, thereby detaching portable plasma module 300 from docking station 350.

Docking station 350 further comprises a station mechanical coupler 370. Station mechanical coupler 370 in the form of a patterned shaft is mechanically associated with the motor of the auxiliary unit 108, possibly via a transmission system, thereby being configured to be rotated by the motor. Station mechanical coupler 370 is further configured to couple to a corresponding module mechanical coupler of the portable plasma module 320 (in FIG. 3A) for transferring the rotational motion of the motor to affect revolution of the table in the plasma chamber.

Docking station 350 further comprises three pairs of station HV connectors 380a1 and 380a2, 380b1 and 380b2, and 380c1 and 380c2. The two station HV connectors in each pair 380x (namely 380a, 380b etc.) are electrically associated with the two poles of one step-up transformer of the auxiliary unit 108. Thus, connectors pair 380a is electrically associated with step-up transformer 184a, and so on. Each HV connector 380 is further configure to electrically connect, upon attachment of docking station 350 to portable plasma module 300, to a corresponding module HV connector of the portable plasma module (330a1, 330a2, . . . 330c2 in FIG. 3A) for electrically associating the step up transformer to a corresponding electrodes pair of the portable plasma module.

Docking station 350 further comprises a station data connector 386, electrically associated with the control unit of the docking station. Data connector 386 is further configured to electrically connect to a corresponding module data connector of the portable plasma module 336 in FIG. 3A, thereby electrically associating sensors or other components in the portable plasma module to the control unit.

Docking station 350 further comprises a station gas port 390, fluidly associated with a fluid channel such as fluid channel 220 in auxiliary unit 108. Station gas port 390 is configured to fluidly associate with a corresponding module gas port of the portable plasma module 340 in FIG. 3A for fluidly associating the interior of the plasma chamber with a vacuum pump or a gas reservoir, as detailed and explained above.

Several or all of the connectors and ports described above—specifically station connector 360, station mechanical coupler 370, station HV connectors 380, station data connector 386 and station gas port 390—may advantageously be located in a station connection area 392 of the docking station, comprising a portion of the external surface of the docking station which contacts the portable plasma module upon connection thereto.

Reverting to FIG. 3A, portable plasma module 300 comprises the module connectors and ports corresponding to the connectors and ports of the docking station described above, for establishing mechanical and functional coupling there between when attached together. Thus, module connector 310 in the form of an eye is configured to connect to the hook of station connector 360 for attaching the portable plasma module to the docking station. Module mechanical coupler 320 is mechanically associated with table 130 via driving wheel 162 and configured to couple with station mechanical coupler 370 for mechanically associating the table with the motor (such as motor 160 in FIG. 1C) of the docking station. 3 pairs of module HV connectors, 330a1 and 330a2, 330b1 and 330b2, and 330c1 and 330c2 are electrically associated with electrodes pairs 120a, 120b and 120c, respectively (for example, module HV connectors 330a1 and 330a2 are connected to electrodes 120a1 and 120a2, respectively, and so on). Thus, each module HV connector is configured to connect with a corresponding station HV connector 380, respectively, for electrically associating a single electrode with one pole of one step-up transformer of the docking station.

Module data connector 336 may be electrically associated with various sensors, electrical units and components of the portable plasma module being thereby configured to provide measurements or indications on operational parameters of the plasma generating system as described above. Module data connector 336 is configured to electrically connect to station data connector 386 upon the attachment of the portable plasma module to the docking station, thereby electrically associating such sensors and components of the portable plasma module to the control unit of the docking station.

Module gas port 340 is fluidly associated with the interior void of the plasma chamber of portable plasma module 300, being configured to fluidly connect to station gas port 390, thereby fluidly associating a gas reservoir or a gas pump of the docking station with the interior of the plasma chamber.

Several or all of the connectors and ports of the portable plasma module—specifically module connector 310, module mechanical coupler 320, module HV connectors 330, module data connector 336 and module gas port 340—may advantageously be located in a module connection area 342 of the portable plasma module, corresponding to and configured to contact with station connection are 393, upon connection to the docking station.

According to some embodiments, portable plasma module 300 may be maintained sterile before and during the plasma treatment, so that a sterile implant may be plasma-treated in the plasma generating system without compromising the implant's sterility, as discussed briefly above. According to some such embodiments, portable plasma module 300 comprises a sterility sleeve 400 depicted in FIG. 3A in a semi-exploded view, departed from plasma chamber 110, in a folded (rolled) state. In the folded state, sterility sleeve 400 may have the form of a short cylinder, a thick ring or a torus, and may be unfolded to obtain the form of a long, flexible and possibly soft tube. Sterility sleeve 400 is located attached to plasma chamber 110, substantially encompassing the module connection area 342. According to some embodiments, sterility sleeve 400 may be unfolded following attachment of portable plasma module 300 to docking station 350 and may be used to encapsulate the docking station therein, so as to ensure maintaining the surroundings of the plasma chamber sterile.

The plasma generating system may be used, according to some embodiments, by carrying out some or all of the following steps: The docking station may be positioned in a non-sterile zone in or near an operating room where implantation is intended to be carried out. The auxiliary unit may be connected to the operation unit, wherein the operation unit is located in a non-sterile zone of the operating room or outside the operating room. The portable plasma module, being sterile, may be placed in a sterile zone of the operating room, and may be opened and, if not already containing the breast implant, be prepared for accepting the breast implant therein. Using sterile hands or tools, the breast implant may be taken out of a sterile package and placed on the table of the plasma chamber. The portable plasma module with the implant therein, may be held by sterile hands or tools and brought over near the docking station, whereas the docking station may also be held by hands or tools not necessarily sterile. The portable plasma module may then be connected to the docking station by attaching the module connection area to the station connection area. Following establishment of connection, the sterility sleeve may be unfolded towards the docking station and further away, to cover and encompass the auxiliary unit and a part or all of the cable from the docking station to the operation unit. Having the sterility sleeve covering substantially all of the docking station with a sterile sleeve, portable plasma module connected to the docking station, may be positioned on a table in a sterile zone, and a plasma treatment session may be started, being commanded and operated from the operation unit, generally by a non-sterile personnel. Following completion of the plasma treatment, the plasma chamber may be opened and the breast implant may be removed from the plasma chamber, by sterile hands or tools, and taken immediately to implantation. The docking station may be taken out of the sterile zone whereas the portable plasma module may be disconnected from the docking station and may be disposed of. Additionally or alternatively the operation unit and possibly the gas reservoir may reside in the sterile zone and may be covered by the sterility sleeve together with the docking station.

The order of some or all of the steps described above may be changed in some embodiments. For example, according to some embodiments, an empty portable plasma module may be connected to the docking station followed by unfolding the sterility sleeve and encapsulating the docking station therewith. The portable plasma module and the docking station connected thereto may then be placed in a sterile region, and then the implant may be placed in the plasma chamber.

Additionally or alternatively, the implant may be transported and delivered to the medical care center within the portable plasma module. According to such embodiments, the portable plasma module with the implant therein may be unpacked and removed from a its package in which it was transported to the medical care center, and may then be taken immediately to a sterile region where it may be connected to the docking station as described above. Plasma treatment and removal of the implant from the plasma chamber for implantation may then follow.

If the portable plasma module is used to plasma-treat the implant a long time before the medical procedure, e.g. at the manufacturing site, then, it is assumed that the implant is stored in the portable plasma module being immersed in a liquid to preserve and retain the beneficial effects of the plasma treatment. In such cases, the implant may be transported to the medical center being stored within the portable plasma module. At the medical care center, soon prior the implantation, the liquid may be drained out of the portable plasma module, e.g. through a liquid drain port. According to some embodiments, liquid port 196 may be used as a liquid drain port. Then the portable plasma module may be opened in a sterile region, and the wet implant may be taken for surgery. There is therefore provided according to an aspect of the invention a method for plasma treating a dielectric implant, comprising applying a plasma-generating electromagnetic (EM) field using at least one electrode so as to generate plasma in a vicinity of the implant while displacing the electrode and the implant relative to one another.

According to some embodiments the implant is inside a closed plasma chamber (110) during the plasma treatment. According to some embodiments the plasma chamber is sealed. According to some embodiments the pressure inside the plasma chamber during plasma treatment is below 1 Atm. According to some embodiments the pressure inside the plasma chamber during plasma treatment is below 0.1 Atm. According to some embodiments the pressure inside the plasma chamber during plasma treatment is not less than 1 Atm. According to some embodiments the composition of the gas inside the chamber is different from air.

According to some embodiments the at least one electrode is stationary and the implant is displaced during the plasma treatment. According to some embodiments the implant is displaced through a rotational motion about a rotation axis. According to some embodiments the rotation axis is vertical. Being stationary or displaceable herein is generally defined relative to Earth.

According to some embodiments the at least one electrode comprises at least one pair of electrodes for applying the plasma-generating electromagnetic (EM) field substantially between the electrodes of the pair. According to some embodiments the at least one pair of electrodes comprises two or more pairs of electrodes. According to some embodiments the average EM power delivered by the electrodes is different from pair to pair.

According to some embodiments the method further comprises a step of wetting the implant by a liquid following the plasma treatment before the implantation. According to some embodiments the liquid is medically effective. According to some embodiments the implant is wetted inside the chamber following the plasma treatment before the implantation. According to some embodiments the implant is displaced in the chamber during the wetting. According to some embodiments the plasma treatment is carried out no more than 10 hours before implanting the implant in a patient. According to some embodiments the implant is stored in liquid after the plasma treatment.

According to some embodiments the implant is a silicone implant. According to some embodiments the implant is a breast implant.

There is further provided according to an aspect of the invention a portable plasma module 300 for plasma treating an implant prior to using the implant in a medical procedure. The portable plasma module comprises a structure (110, 112, 114) and at least one electrode (120) fixed to the structure and configured to apply a plasma-generating electromagnetic (EM) field for generating plasma in a vicinity of the electrode. The portable plasma module further comprises a table (130) configured to support the implant, the table being mechanically associated with the structure so as to enable the table and the structure to constrictively displace relative to one another. The portable plasma module further comprises a module mechanical coupler (320) configured to mechanically associate with a motor (160), to allow displacing the table and the structure relative to one another. The portable plasma module further comprises at least one module electrical connector (330) configured to electrically associate an EM power source (e.g. HV power source 180 in FIG. 2) to the at least one electrode to apply the plasma-generating electromagnetic (EM) field by the electrode. According to some embodiments the module electrical connector is a HV connector. According to some embodiments the electrical connector is a low voltage connector, the power source is a low voltage power source, and transformation of the low voltage to a high voltage sufficient for plasma generation is carried out at the portable plasma module. According to some embodiments such transformation may be carried out by a voltage transformer piezoelectric element attached to the portable plasma module.

According to some embodiments the portable plasma module further comprises a plasma chamber (110) dimensioned and configured to house the implant therein during the plasma treatment.

According to some embodiments the structure is fixed to the plasma chamber and the table is displaceable relative thereto. According to some embodiments the table is displaceable in a rotational motion around a vertical axis of rotation (192). According to some embodiments the plasma chamber is configured to be sealed. According to some embodiments the plasma chamber comprises a liquid port (196) for injecting liquid into the plasma chamber. According to some embodiments the liquid port may be used to drain liquid from the plasma chamber. According to some embodiments the portable plasma module is configured to store the implant following the plasma treatment, being immersed in liquid, for more than a day.

According to some embodiments the portable plasma module further comprises a module connector (310) configured to connect to a corresponding docking station connector (360) of a docking station (350), for attaching the portable plasma module to the docking station.

According to some embodiments the portable plasma module further comprises a module data connector (336) configured to connect to a corresponding station data connector (386) of the docking station. According to some embodiments the portable plasma module further comprises a module gas port (340) fluidly associated with the interior void of the plasma chamber (110).

According to some embodiments the table (130) has a support aspect ratio smaller than about 20%.

According to some embodiments the portable plasma module further comprises a sterility sleeve (400) configured, in an unfolded state, to encapsulate the docking station (350) when the docking station is connected to the portable plasma module.

There is further provided according to an aspect of the invention a docking station (350) configured to connect to the portable plasma module (300) to enable generation of plasma therein. The docking station comprises a station electric connector (380) electrically associated with an EM power source (such as, for example, 180 in FIG. 2) and configured to electrically associate with a module electrical connector (330) of the portable plasma module (300), thereby transferring from the EM power source EM power sufficient to generate plasma in a vicinity of the electrode(s) thereof. The docking station further comprises a station mechanical coupler (370) mechanically associated with a motor (such as motor 160 in FIG. 1C), and is configured to connect to a module mechanical coupler (310) of the portable plasma module thereby transferring a rotation motion of the station mechanical coupler to a rotational motion of the module mechanical coupler.

According to some embodiments the docking station further comprises a step-up transformer (184) electrically associated via an output thereof with the station electric connector and configured to receive a low voltage RF signal from a low voltage signal generator (186) and produce on the output a HV RF signal.

According to some embodiments the docking station further comprises a station mechanical connector (360) configured to connect to a corresponding module mechanical connector (310) of the portable plasma module, for attaching the portable plasma module to the docking station. According to some embodiments the docking station further comprises a station data connector (386) configured to connect to a corresponding module data connector (336) of the portable plasma module. According to some embodiments the docking station further comprises a station gas port (390) configured to connect to a corresponding module gas port (340) of the portable plasma module.

There is further provided according to an aspect of the invention a plasma generation system comprising the portable plasma module (300) and the docking station (350). According to some embodiments the plasma generation system further comprises an operation unit (200) comprising an operation panel (210), electrically associated with the docking station and configured to enable a user commanding the plasma generating system through the operation panel, and/or to obtain operational data therethrough.

There is further provided according to an aspect of the invention a plasma generating apparatus (100) for treating an implant prior to using the implant in a medical procedure. The plasma generating apparatus comprises a structure (110, 112, 114) and at least one electrode (120) fixed to the structure and configured to apply a plasma-generating electromagnetic (EM) field for generating plasma in a vicinity thereof. The plasma generating apparatus further comprises an EM power source electrically associated with the electrode. The plasma generating apparatus further comprises a table (130) mechanically associated with the structure so as to enable the table and the structure to constrictively displace relative to one another, the table being configured to support the implant. The plasma generating apparatus further comprises a motor (16) mechanically associated with the structure and with the table, being thereby configured to displace the structure and the table one relative to the other. The plasma generating apparatus further comprises an operation unit 200 functionally associated with the EM power source and possibly with the motor, being configured to control the operation of the EM power source and the motor and further comprising an operation panel (210) enabling an operator commanding the plasma treatment apparatus.

According to some embodiments the EM power source is a HV power source (180). According to some embodiments the electrode is an edge of a voltage transformer piezoelectric element and the power source is a low voltage (typically high-current) signal generator (182).

According to some embodiments the plasma generating apparatus further comprises a plasma chamber (110). According to some embodiments the plasma chamber is configured to be sealed. According to some embodiments the plasma generating apparatus further comprises a vacuum pump (222) fluidly associated to the plasma chamber. According to some embodiments the plasma generating apparatus further comprises a gas port configured to fluidly connect to a gas reservoir to flow gas to the plasma chamber.

According to some embodiments the table is stationary and the at least one electrode is displaced during the plasma treatment. According to some embodiments the at least one electrode is stationary and the table is displaced during the plasma treatment. According to some embodiments the table is displaced through a rotational motion about a rotation axis.

According to some embodiments the at least one electrode comprises at least one pair of electrodes (120a, 120b, 120c) for applying the plasma-generating electromagnetic (EM) field substantially between the electrodes of the pair. According to some embodiments the at least one pair of electrodes comprises two or more pairs of electrodes. According to some embodiments the average EM power delivered by the electrodes is different from pair to pair.

According to some embodiments the plasma chamber comprises a liquid port (196) for injecting liquid into the plasma chamber, to wet the implant or to immerse the implant in the liquid. According to some embodiments the table is configured to controllably displace while the implant is wetted inside the chamber.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A portable plasma module for plasma treating an implant prior to using the implant in a medical procedure, the portable plasma module comprising:
    a structure;
    at least one electrode fixed to the structure and configured to apply a plasma-generating electromagnetic (EM) field for generating plasma in a vicinity of the at least one electrode;
    a table configured to support the implant, the table being mechanically associated with the structure so as to enable the table and the structure to constrictively displace relative to one another;
    a module mechanical coupler configured to connect the portable plasma module to a transmission unit associated with a motor, to allow displacing the table and the structure relative to one another; and
    at least one module electrical connector configured to electrically associate an EM power source to the at least one electrode to apply the plasma-generating electromagnetic (EM) field by the electrode.

2. The portable plasma module of claim 1 wherein the at least one module electrical connector includes a HV connector.

3. The portable plasma module of claim 1, further comprising a plasma chamber fixed to the structure and dimensioned and configured to house the implant therein during the plasma treatment, and the table is displaceable relative thereto.

4. The portable plasma module of claim 3 wherein the plasma chamber includes a liquid port for injecting liquid into the plasma chamber.

5. The portable plasma module of claim 3, further comprising a module gas port fluidly associated with the interior void of the plasma chamber.

6. The portable plasma module of claim 1, further comprising a module connector configured to connect to a corresponding docking station connector of a docking station, for attaching the portable plasma module to the docking station.

7. The portable plasma module of claim 6, further comprising a sterility sleeve configured, in an unfolded state, to encapsulate the docking station when the docking station is connected to the portable plasma module.

8. The portable plasma module of claim 1, further comprising a module data connector configured to connect to a corresponding station data connector of a docking station.

9. A docking station configured to connect to a portable plasma module to enable generation of plasma therein, the docking station comprising:
    a station electric connector electrically associated with an electromagnetic (EM) power source and configured to electrically associate with a module electrical connector of a portable plasma module having a plasma chamber, thereby transferring from the EM power source EM power sufficient to generate plasma in the plasma chamber; and
    a station mechanical coupler mechanically associated with a motor, configured to connect to a module mechanical coupler of the portable plasma module thereby transferring a rotation motion of the station mechanical coupler to a rotational motion of the module mechanical coupler.

10. The docking station of claim 9, further comprising a step-up transformer electrically associated via an output thereof with the station electric connector and configured to receive a low voltage RF signal from a low voltage signal generator and produce on the output a HV RF signal.

11. The docking station of claim 9, further comprising a station mechanical connector configured to connect to a corresponding module mechanical connector of the portable plasma module, for attaching the portable plasma module to the docking station.

12. The docking station of claim 9, further comprising a station data connector configured to connect to a corresponding module data connector of the portable plasma module.

13. The docking station of claim 9, further comprising a station gas port configured to connect to a corresponding module gas port of the portable plasma module.

14. A plasma generating apparatus for treating an implant prior to using the implant in a medical procedure, the plasma generating apparatus comprising:

a structure;

at least one electrode fixed to the structure and configured to apply a plasma-generating electromagnetic (EM) field for generating plasma in a vicinity thereof;

an EM power source electrically associated with the at least one electrode;

a table mechanically associated with the structure so as to enable the table and the structure to constrictively displace relative to one another, the table being configured to support the implant;

a motor mechanically associated with the structure and with the table, being thereby configured to displace the structure and the table one relative to the other, and an operation unit functionally associated with the EM power source and with the motor, configured to control the operation of the EM power source and the motor and further comprising an operation panel enabling an operator commanding the plasma generating apparatus.

15. The plasma generating apparatus of claim 14 wherein the EM power source includes high voltage (HV) power source.

16. The plasma generating apparatus of claim 14 wherein the at least one electrode includes an edge of a voltage transformer piezoelectric element and the EM power source includes a low voltage signal generator.

17. The plasma generating apparatus of claim 14 wherein the at least one electrode is stationary and the table is displaced during the plasma treatment.

18. The plasma generating apparatus of claim 14, further comprising a plasma chamber and a vacuum pump fluidly associated with the plasma chamber.

19. The plasma generating apparatus of claim 18, further comprising a gas port configured to fluidly connect to a gas reservoir to flow gas to the plasma chamber.

20. The plasma generating apparatus of claim 18 wherein the plasma chamber includes a liquid port for injecting liquid into the plasma chamber.

21. The plasma generating apparatus of claim 20 wherein the table is configured to controllably displace while the implant is wetted inside the chamber.

* * * * *